United States Patent [19]
Kuth et al.

[11] Patent Number: 5,663,646
[45] Date of Patent: Sep. 2, 1997

[54] HEAD ANTENNA FOR NUCLEAR MAGNETIC RESONANCE EXAMINATIONS

[75] Inventors: Rainer Kuth, Herzogenaurach; Michael Knauth, Neuisenburg; Rainer Wirtz, Edingen; Reiner Henkelmann, Erlangen; Rudolf Moder, Neumarkt; Wilhelm Duerr, Erlangen, all of Germany

[73] Assignee: Siemens Aktiengesellschaft, Munich, Germany

[21] Appl. No.: 624,913

[22] Filed: Mar. 27, 1996

[30] Foreign Application Priority Data

Mar. 30, 1995 [DE] Germany .......... 195 11 796.4

[51] Int. Cl.$^6$ .................................................. G01V 3/00
[52] U.S. Cl. ........................................ 324/318; 128/653.5
[58] Field of Search ............................... 324/318, 322, 324/321, 314, 307, 309, 300; 128/653.5

[56] References Cited

U.S. PATENT DOCUMENTS

| | | |
|---|---|---|
| 4,706,665 | 11/1987 | Gouda . |
| 4,791,372 | 12/1988 | Kirk et al. ............... 324/322 |
| 4,923,459 | 5/1990 | Nambu . |
| 5,007,425 | 4/1991 | Vanek et al. . |
| 5,085,219 | 2/1992 | Ortendahl et al. ........... 324/318 |
| 5,274,332 | 12/1993 | Jaskolski et al. ........... 324/318 |
| 5,357,958 | 10/1994 | Kaufman . |
| 5,379,767 | 1/1995 | Derby et al. ............... 324/318 |
| 5,380,336 | 1/1995 | Misko et al. . |
| 5,519,321 | 5/1996 | Hagen et al. . |

FOREIGN PATENT DOCUMENTS

| | | |
|---|---|---|
| 0 623318 | 11/1994 | European Pat. Off. . |
| OS 3822185 | 1/1989 | Germany . |
| OS 3934919 | 4/1990 | Germany . |
| OS 3932648 | 4/1991 | Germany . |
| PS 3500456 | 9/1994 | Germany . |

OTHER PUBLICATIONS

"Hochfrequenzsysteme für die Kernspintomografie," Dürr et al., ntzArchiv, vol. 11, No. 5 (1989), pp. 237–243 75.

"Stereotaxic Biopsy of the Brain under MR Imaging Control," Thomas et al., AJNR, vol. 7, Jan./Feb. 1996, pp. 161–163.

*Primary Examiner*—Louis M. Arana
*Attorney, Agent, or Firm*—Hill, Steadman & Simpson

[57] ABSTRACT

A head antenna for nuclear magnetic resonance examinations has an examination chamber, formed so as to accept the head, and an antenna conductor, formed as a frame antenna, that surrounds the examination chamber in an examination position. The antenna conductor is divided into two curved sub-conductors that respectively have electrical contacts at their ends for detachably electrically connecting the sub-contractors together. The first sub-conductor arrangement is fastened to a holding part which is arranged outside the examination chamber and which is made of an electrically non-conductive, non-ferromagnetic material. For fastening the holding part to a patient support, a first fastening assembly is arranged on the holding part. For fixing the position of the head, a second fastening assembly is arranged on the holding part.

21 Claims, 2 Drawing Sheets

HEAD ANTENNA FOR NUCLEAR MAGNETIC RESONANCE EXAMINATIONS

BACKGROUND OF THE INVENTION

1. Field of the Invention

The present invention is directed to a head antenna for nuclear magnetic resonance examinations of the head in the context of surgical operations in the head area, the head antenna being of the type having an examination chamber formed so as to accept the head and an antenna conductor formed as a frame antenna that surrounds the examination chamber in an examination position.

2. Description of the Prior Art

A head antenna of the general type described above is known from German OS 43 18 134. The antenna has an antenna conductor formed as a frame antenna. After the positioning the head on a patient-supporting surface of a patient positioning means, the vertically oriented frame antenna is displaced parallel to the patient positioning means until the head is located in the examination chamber of the antenna.

If nuclear magnetic resonance examinations are to be carried out during neurosurgical operations, it is necessary that the head be held stable, in order to ensure, first, that the position of the head does not change during the operation, and to cushion the forces that arise, in particular, during the production of a burr hole in the skull. During neurosurgical operations, head mounts are thus employed that include fastening means for fixing the head. A head mount that can also be used in connection with nuclear magnetic resonance examinations is described in the article "Stereotaxis Biopsy of the Brain under MR Imaging Control," by D. G. T. Thomas, C. H. Davis. S. Ingram, J. S. Olney, G. M. Bydder and I. R. Young, in AJNR 7: 161–163, January/February 1986. The mount is made of non-ferromagnetic materials. Moreover, in the mounting frame no closed metallic loops, which could cause eddy currents, are used. In addition, markings which are visible in the nuclear magnetic resonance image are attached to the head mount, by means of which a precise correlation of the nuclear magnetic resonance image to the patient's anatomy is made possible. Before the actual operation, a receiving antenna for nuclear magnetic resonance imaging is arranged around the holder. The examination chamber of this receiving antenna is larger than that of a normal head antenna, because both the head and the head mount must be housed therein. For this reason, the fullness factor, and thus also the signal-noise ratio, is worse in comparison with a normal head antenna. Moreover, the use of this known arrangement during the actual surgical procedure is complicated, due to the accessibility required and the demands of a sterile operating environment.

SUMMARY OF THE INVENTION

An object of the present invention is to provide a head antenna for use in obtaining magnetic resonance images that ensures a stable holding of the patient's head in the context of neurosurgical operations.

This object is achieved in accordance with the principles of the present invention in a head antenna having an antenna conductor which is divided into two curved sub-conductors, each having an end with an electrical contact for connecting the sub-conductors together, the first sub-conductor being fastened to a holding part which is arranged outside the examination chamber and which is made of an electrically non-conductive, non-ferromagnetic material and, for fastening the holding part to a patient positioning means, first fastening means are arranged on the holding part, and for fixing the head, second, separate fastening means are arranged on the holding part. During the entire neurosurgical operation, the patient's head remains fixed in the holding part. The second sub-conductor is removed during the surgical operation, so that the surgeon's access to the patient is not hindered. If the generation of a nuclear magnetic resonance image is required during the surgical operation, the operation is interrupted, and the second sub-conductor is attached to the fixed first sub-conductor. In this way the frame antenna is completed, and the head of the patient can be imaged in a nuclear magnetic resonance apparatus with the highest image quality. The upper sub-conductor is subsequently removed, and the operation can continue.

In one embodiment, the second sub-conductor is sheathed with a sterilizable plastic. The head antenna is thus usable without additional protective measures such as, for example, enveloping with removable sterile coverings.

In a further embodiment, the second sub-conductor is formed so as to be flexible. The second sub-conductor is thereby easily connected and disconnected and additionally can be adapted in situ to the anatomy.

In another embodiment, the first sub-conductor is arranged on at least one lateral surface of the holding part. By virtue of the structural unity of the sub-conductor with the holding part, the head antenna is easily assembled and handled.

In a further embodiment, the holding part is annular and surrounds the examination chamber. This structural embodiment of the holding part enables a particularly high degree of sturdiness and stability with a low material expenditure.

In another embodiment, a holding ring is arranged on the holding part, to which operating instruments such as e.g. skin retractors and the like may be fastened.

DESCRIPTION OF THE PREFERRED EMBODIMENTS

Figure 1:
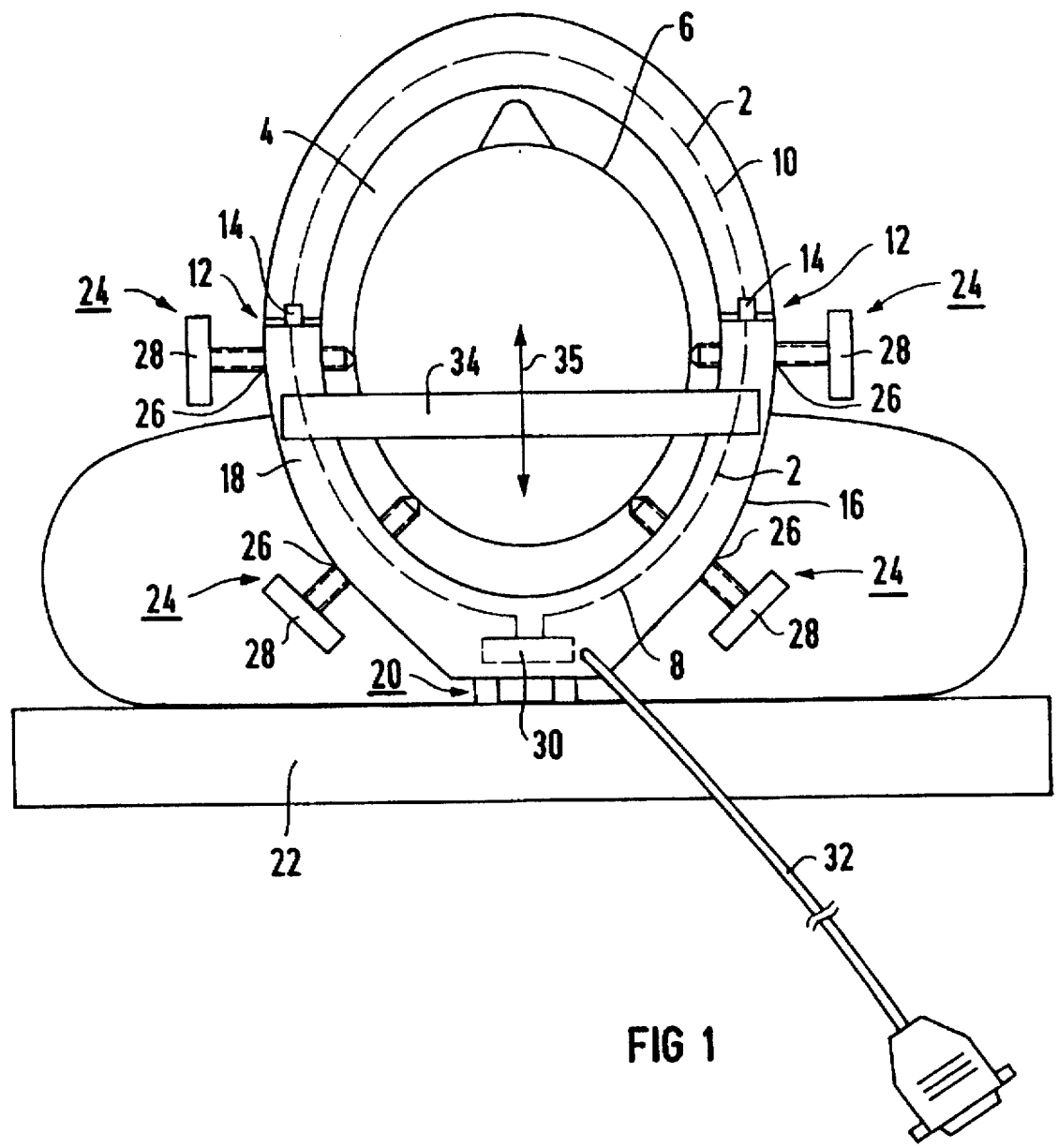
FIG. 1 shows a first embodiment of a head antenna in an axial view in accordance with the principles of the present invention.

The head antenna represented in an axial view in FIG. 1 is intended for use in nuclear magnetic resonance devices having a main static magnetic field oriented perpendicularly to the longitudinal axis of a patient, e.g. vertically. The head antenna includes an antenna conductor 2 formed as a frame antenna having one or more coil turns. The antenna conductor 2 defines, in an examination position suited for nuclear magnetic resonance examinations, an examination chamber 4 having rounded cross-section (i.e., circular to oval and variations in between), dimensioned so that it can accept the head 6 of a patient. The frame antenna is preferably formed ellipsoidally. In order to avoid hindering access for surgical operations, the antenna conductor 2 is divided into two curved sub-conductor arrangements 8 and 10 of about the same size, each having an end 12 at which a gold-plated electrical contacts 14 is disposed for detachably electrically connecting the sub-conductor arrangements 8 and 10 together. In other words, the two sub-conductor arrangements 8 and 10 are essentially formed as half-rings. The first sub-conductor arrangement 8 is fastened to two lateral surfaces 18 of a holding part 16, which is likewise curved around the examination chamber 4.

The holding part 16 is made of a mechanically heavy-duty, electrically non-conductive, non-ferromagnetic material having good high-frequency characteristics, such as e.g. plastic, glass-fiber reinforced plastic (GFK) or ceramic. The high-performance polymer polybenzimidazol (PBI), available as a molded part from the company Ensinger in Nufringen, Germany, is particularly well-suited.

The holding part 16 has a first fastening assembly 20 in the form of plug pins, permitting the holding part 16 to be fastened to a patient positioning support 22 in a perpendicular orientation. For fixing the position of the head 6, a second fastening assembly 24 is arranged in the holding part 16. The second fastening assembly 24 includes bone screws 28 screwable into threaded holes 26, which screws 28 have a sterilizable tip. The bone screws 28 are made of a non-ferromagnetic material such as e.g. titanium. The tip or spike, which penetrates into the cranial bone of the patient, is separated from the threaded part of the bone screw 38 by an electrically insulating layer (not shown), in order to shield the patient from electrical voltages that may arise during the nuclear magnetic resonance examination.

The second sub-conductor arrangement 10 is preferably constructed so as to be flexible and is sheathed by a flexible, sterilizable plastic made of, e.g., the above-described polybenzimidazol. The sterile second sub-conductor arrangement 10 considerably simplifies the handling of the head antenna when the skull is open. The first sub-conductor arrangement 8 is also covered with a plastic that is at least disinfectable.

In or on the holding part 16, tuning and matching circuits 30 are housed, to which a connection line 32 leads for connecting the antenna conductor 2 with the actual nuclear magnetic resonance apparatus.

A holding bow 34 made of plastic can be fastened to the holding part 16 at some predetermined positions. The holding bow 34 is intended to hold operating aids such as skin retractors and the like. The holding bow 34 is therefore additionally adjustable in position, as represented by a double arrow 35.

Figure 2:
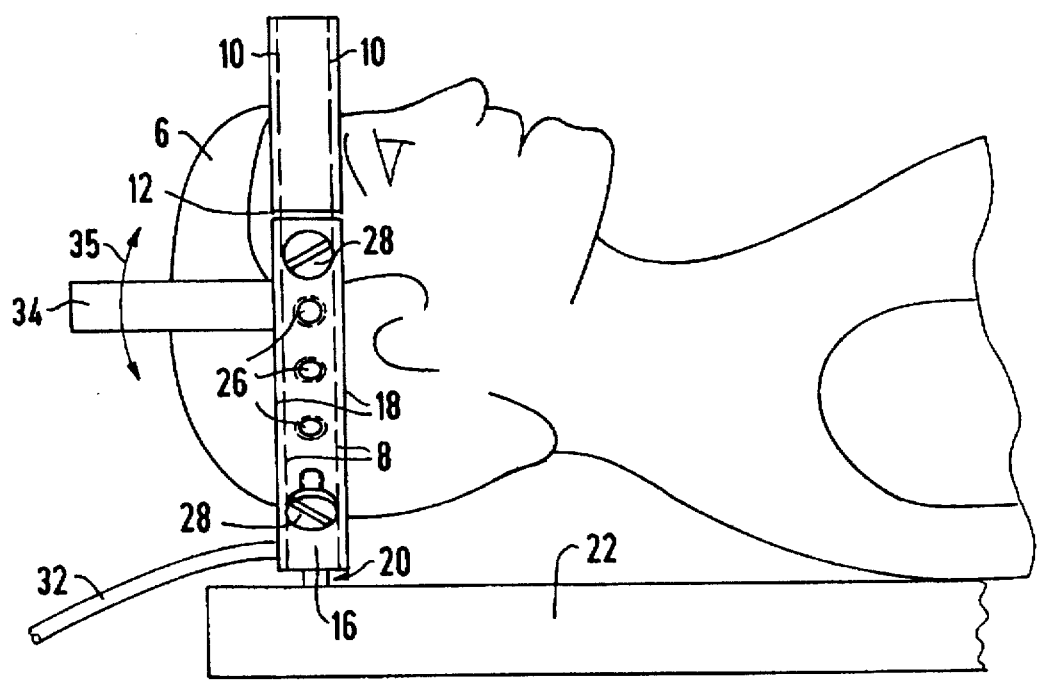
FIG. 2 shows a side view of the antenna according to FIG. 1.

FIG. 2 shows a side view of the head antenna according to FIG. 1. As can be seen in FIG. 2, the antenna conductor 2 has two coil turns, which are continuous when the sub-conductor arrangements 8 and 10 are connected via the contacts 14. The coil turns are respectively fastened to front and rear lateral surfaces 18 of the holding part 16.

Figure 3:
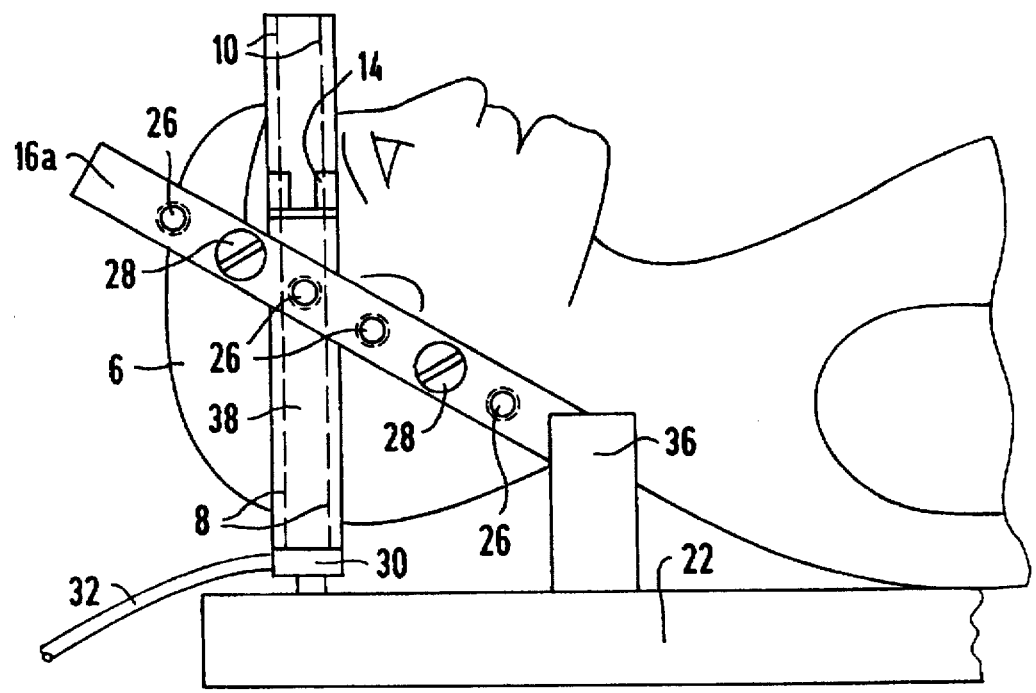
FIG. 3 shows a side view of a second embodiment of a head antenna constructed in accordance with the principles of the present invention.

In the second embodiment of the neurosurgical head antenna, shown in a side view in FIG. 3, the holding part 16a is annular and is fastenable at an angle to the patient positioning support 22. Again, a second fastening assembly 24 is provided in the holding part 16a for fixing the head. The attachment of the holding part 16a to the patient support 22 takes place via a mount 36. In contrast to the embodiment according to FIGS. 1 and 2, the first sub-conductor arrangement 8 is arranged on a carrier 38 by which the holding part 16a passes. The carrier 38 is in turn fastened to the holding part 16a and is oriented perpendicularly to the patient positioning support 22.

The sheathed sub-conductor 10 is in this embodiment also covered with a sterilizable plastic. The remaining parts of the head antenna are at least sheathed with a disinfectable material or are themselves made of a disinfectable material.

Although modifications and changes may be suggested by those skilled in the art, it is the intention of the inventors to embody within the patent warranted hereon all changes and modifications as reasonably and properly come within the scope of their contribution to the art.

We claim as our invention:

1. A head antenna for conducting a nuclear resonance examination of the head of a patient, the patient being disposed on a patient support, during a surgical procedure in a region of the head, said head antenna comprising:

a frame antenna defining an examination chamber adapted for accepting said head;

said frame antenna comprising an antenna conductor divided into first and second curved sub-conductors each having two free ends, each sub-conductor having an electrical contact at each end for detachably electrically connecting said first and second sub-conductors together;

a holder for said first sub-conductor disposed outside of said examination chamber comprised of electrically non-conductive, non-ferromagnetic material;

first fastening means for attaching said holder to said patient support;

second fastening means adapted for fixing the head of said patient relative to said holder; and said frame antenna, said holder, said first fastening means and said second fastening means together forming assembly means for simultaneously rigidly holding the head of the patient during a surgical procedure requiring opening of the skull, allowing access to an opened skull region, and allowing a magnetic resonance head imaged to be obtained during surgical procedure with said assembly means being substantially invisible in said image.

2. A head antenna as claimed in claim 1 wherein said second fastening means comprise bone screws and threaded holes in said holder assembly respectively receiving said bone screws.

3. A head antenna as claimed in claim 1 further comprising a sheathing of sterilizable plastic on said second sub-conductor.

4. A head antenna as claimed in claim 1 wherein said second sub-conductor comprises a flexible sub-conductor.

5. A head antenna as claimed in claim 1 wherein said second fastening means comprise means for orienting said frame antenna perpendicularly to said patient support.

6. A head antenna as claimed in claim 1 wherein said frame antenna comprises an ellipsoidally-shaped frame antenna.

7. A head antenna as claimed in claim 1 wherein said holder is curved.

8. A head antenna as claimed in claim 7 wherein said holder has a lateral edge and wherein said first sub-conductor is disposed on said lateral edge.

9. A head antenna as claimed in claim 1 wherein said first fastening means comprise means for orienting said holder perpendicularly relative to said patient support.

10. A head antenna as claimed in claim 1 wherein said holder is annular and surrounds said examination chamber.

11. A head antenna as claimed in claim 10 wherein said holder assembly is oriented at a non-zero angle relative to said frame antenna.

12. A head antenna as claimed in claim 1 further comprising a bow adapted to surround a top of said head, attached to said holder.

13. A head antenna as claimed in claim 1 wherein each of said sub-conductors is semi-circular.

14. A head antenna for conducting a nuclear magnetic resonance examination of the head of a patient, said patient being disposed on a patient support, during a surgical procedure in a region of the head, said head antenna comprising:
- a frame antenna having an examination chamber adapted to receive the head, said frame antenna having an antenna conductor divided into first and second curved, separable sub-conductors, each sub-conductor having two free ends and each free end of each sub-conductor having an electrical contact for detachably electrically connecting said first and second sub-conductors together;
- said frame antenna having a lower part carrying said first sub-conductor and an upper part, detachable from said lower part, carrying said second sub-conductor;
- first fastening means for attaching said lower part to said patient support;
- second fastening means, carried by said lower part, for fixing a position of said head relative to said lower part; and
- said frame antenna, said first fastening means and said second fastening means together forming assembly means for simultaneously rigidly holding the head of the patient during a surgical procedure requiring opening of the skull, allowing access to an opened skull region, and allowing a magnetic resonance head imaged to be obtained during surgical procedure with said assembly means being substantially invisible in said image.

15. A head antenna as claimed in claim 14 wherein said first fastening means comprise means for orienting said lower part perpendicularly relative to said patient support.

16. A head antenna for conducting a nuclear magnetic resonance examination of the head of a patient, said patient being disposed on a patient support, during a surgical procedure in a region of the head, said head antenna comprising:
- a frame antenna having an examination chamber adapted to receive said head, said frame antenna having an antenna conductor comprising first and second separable sub-conductors, each sub-conductor having two free ends and an electrical contact disposed at each free end for detachably electrically connecting said first and second sub-conductors together;
- said frame antenna having a lower part carrying said first sub-conductor and an upper part, detachable from said lower part, carrying said second sub-conductor;
- first fastening means for attaching said lower part to said patient support;
- an annular holder adapted to surround the head of said patient and attached at a non-zero angle to said lower part;
- second fastening means, carded by said holder, for fixing a position of the head of said patient relative to said holder and said lower part; and
- said frame antenna, said holder, said first fastening means and said second fastening means together forming assembly means for simultaneously rigidly holding the head of the patient during a surgical procedure requiring opening of the skull, allowing access to an opened skull region, and allowing a magnetic resonance head imaged to be obtained during surgical procedure with said assembly means being substantially invisible in said image.

17. A head antenna as claimed in claim 16 wherein said first fastening means comprise means for orienting said lower part perpendicularly relative to said patient support.

18. A head antenna as claimed in claim 16 further comprising third fastening means for fastening said holder to said patient support.

19. A head antenna as claimed in claim 1 wherein said frame antenna is band-shaped.

20. A head antenna as claimed in claim 14 wherein said frame antenna is band-shaped.

21. A head antenna as claimed in claim 16 wherein said frame antenna is band-shaped.

* * * * *